United States Patent
Isaac et al.

(10) Patent No.: US 6,687,543 B1
(45) Date of Patent: Feb. 3, 2004

(54) IMPLANTABLE CARDIAC STIMULATION DEVICE HAVING REDUCED SHELF CURRENT CONSUMPTION AND METHOD

(75) Inventors: George I. Isaac, Port Hueneme, CA (US); Alan B. Vogel, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 300 days.

(21) Appl. No.: 09/876,725

(22) Filed: Jun. 6, 2001

(51) Int. Cl.$^7$ ................................................. A61N 1/08
(52) U.S. Cl. ........................................................ 607/16
(58) Field of Search ................................ 607/2, 16, 30, 607/34, 60

(56) References Cited

U.S. PATENT DOCUMENTS

| | | | |
|---|---|---|---|
| 4,390,022 A | * | 6/1983 | Calfee et al. ................. 607/16 |
| 5,215,086 A | * | 6/1993 | Terry et al. ................... 607/46 |
| 5,350,407 A | | 9/1994 | McClure et al. .............. 607/16 |
| 5,370,666 A | | 12/1994 | Lindberg et al. .............. 607/16 |
| 5,476,485 A | | 12/1995 | Weinberg et al. ............. 607/28 |
| 5,522,856 A | * | 6/1996 | Reineman ...................... 607/9 |
| 6,016,448 A | | 1/2000 | Busacker et al. ............. 607/29 |
| 6,223,080 B1 | * | 4/2001 | Thompson ..................... 607/16 |
| 6,453,198 B1 | * | 9/2002 | Torgerson et al. ............ 607/29 |
| 2003/0065370 A1 | * | 4/2003 | Lebel et al. ................... 607/60 |

* cited by examiner

Primary Examiner—Kennedy Schaetzle

(57) ABSTRACT

A processor controlled implantable cardiac stimulation device may be placed into a shelf mode for extending the shelf life of the device. The device includes a real time clock circuit, a watch dog timer circuit having a duty cycle, a telemetry circuit capable of operation in either an active mode or a standby mode, and ancillary circuits that sense cardiac activity and provides stimulation pulses to a heart. The device includes a power source for providing power to all of the circuits of the device and a shelf mode circuit that places the device into the shelf mode. The shelf mode circuit disables power to the ancillary circuits, decreases the duty cycle of the watch dog timer, sets the processor into a static state, and sets the telemetry circuit to the standby mode. The shelf mode circuit places the device into the shelf mode in response to shelf mode commands received by the telemetry circuit to set the device from an active powered mode to the shelf mode.

20 Claims, 6 Drawing Sheets

IMPLANTABLE CARDIAC STIMULATION DEVICE HAVING REDUCED SHELF CURRENT CONSUMPTION AND METHOD

FIELD OF THE INVENTION

The present invention is generally directed to an implantable cardiac stimulation device which is powered by a depletable power source. The present invention is more particularly directed to such a device which provides reduced shelf current consumption prior to implant.

BACKGROUND OF THE INVENTION

Implantable cardiac stimulation devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac stimulation devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Since implantable cardiac stimulation devices are implanted beneath the skin of a patient, they are powered by a depletable power source, such as a battery. When the remaining battery energy capacity falls below a certain limit, referred to as end of life (EOL), the device must be replaced. Further, prior to EOL, as for example 90 days prior to EOL, the battery will reach a remaining energy capacity corresponding to the recommended replacement time (RRT). An RRT indication is generally provided to alert the patient's physician that EOL is imminent and is timed relative to EOL to afford the physician sufficient time to schedule replacement of the device before EOL is reached.

As may be discerned from the above, the rate of power consumption by the implanted device is an important consideration after the device is implanted. However, of equal importance and often overlooked is the power consumption by the implantable device after manufacture but before implant.

Implantable cardiac devices are essentially all controlled by internal controllers such as microprocessors. They are in turn controlled by downloaded software. After a device is manufactured and downloaded with software, it is fully tested. Once fully tested, it is then placed into a "shelf" mode by a non-implantable device, such as a programmer, for operation in a low power consumption shelf mode.

Existent techniques of placing implantable pacemakers into a shelf mode result in shelf mode battery consumption currents on the order of 8 $\mu$a. With modern day battery technology, this permits a shelf life on the order of one year with a total battery depletion of about 70 mAH. With respect to defibrillators, shelf life on the order of also one year may be expected with a total battery consumption on the order of 104 mAH. This represents the total consumption of 16 mAH for capacitor reformation and 88 mAH for general consumption.

As will be seen hereinafter, the present invention decreases the shelf current consumption to such a small level that it ceases to become a significant factor in determining device longevity. For example, a shelf current consumption of 1 $\mu$a will deplete the battery of a pacemaker by 70 mAH over 8 years, and 104 mAH for a defibrillator over 4 years. The battery self discharge dominates battery depletion for shelf currents of 1 $\mu$A or less.

SUMMARY OF THE INVENTION

The present invention provides a processor controlled implantable cardiac stimulation device having reduced shelf current consumption. In accordance with the broader aspects of the present invention, a shelf mode is established within the device by disabling power to all device circuits except a real time clock, a watch dog timer, a telemetry circuit and the processor which is placed into a static state. The telemetry circuit is placed into a standby mode and the duty cycle of the watch dog timer is reduced. The standby mode of the telemetry circuit permits the telemetry circuit to receive commands from an external source for returning the device to a fully powered active mode prior to or during implant.

When the invention is embodied in an implantable defibrillator, the fully powered active mode may be restored periodically for capacitor reformation. Once the capacitors are charged, the device may then be returned to the shelf mode.

The real time clock times capacitor reform periods and keeps track of time related information. When it is time to reform the capacitors, the real time clock initiates the return to the fully powered active mode and/or the capacitor reformation mode.

When the device is in the shelf mode, the watch dog timer detects for microprocessor errors. If a microprocessor error is detected, the device is returned to the fully powered active mode as an alert to the error condition.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
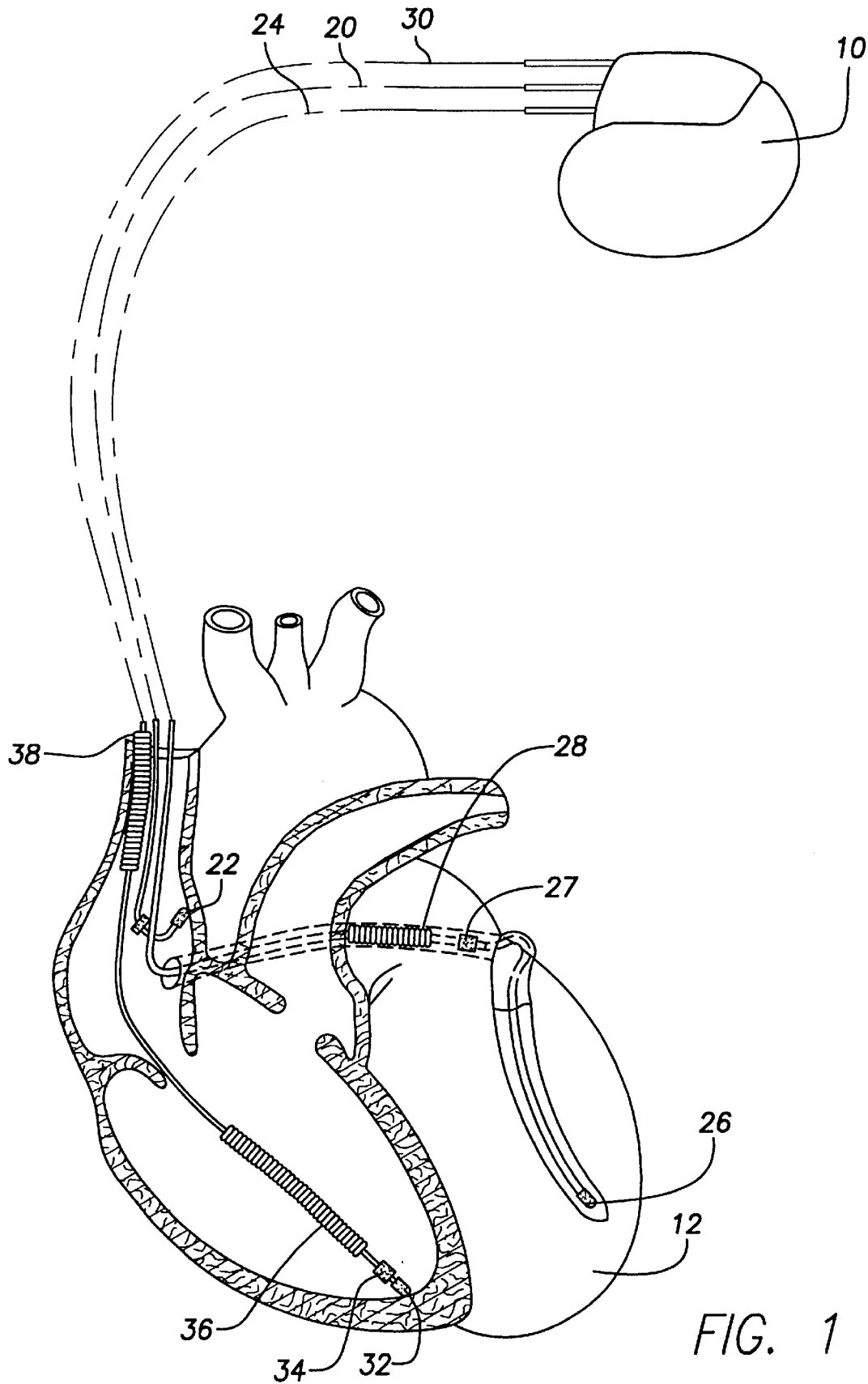
FIG. 1 is a simplified diagram illustrating an implantable cardiac stimulation device in electrical communication with one or more leads implanted into a patient's heart for delivering multi-chamber or single chamber stimulation and/or shock therapy.

As shown in FIG. 1, there is a stimulation device 10 in electrical communication with a patient's heart 12 by way of three leads, 20, 24 and 30, suitable for delivering multi-chamber stimulation and shock therapy. The device 10 also embodies the present invention for placing the device into an improved shelf mode resulting in reduced shelf current consumption.

To sense atrial cardiac signals and to provide right atrial chamber stimulation therapy, the stimulation device 10 is coupled to an implantable right atrial lead 20. The right atrial lead 20 has at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the ostium of the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
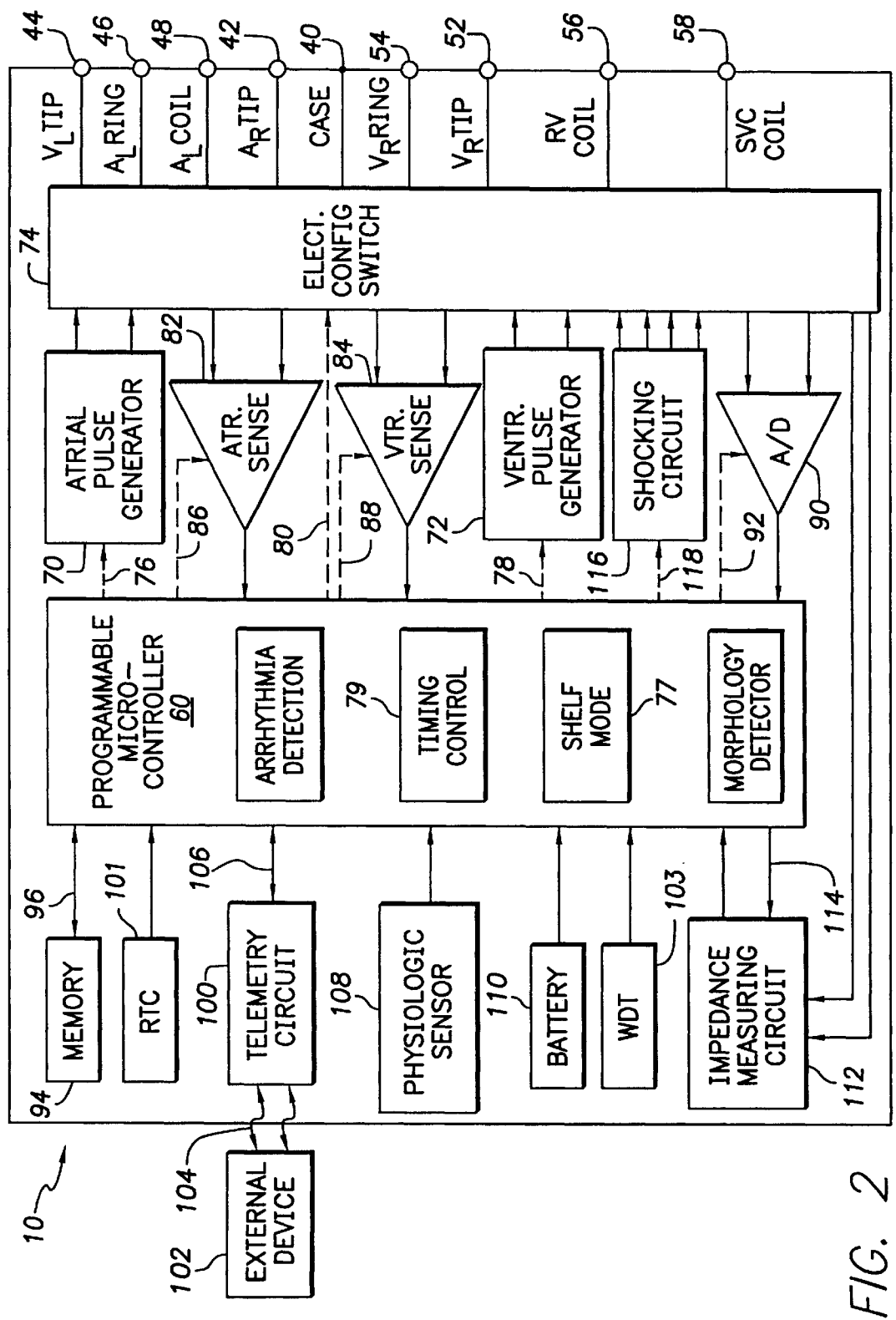
FIG. 2 is a functional block diagram of a multi-chamber implantable cardiac stimulation device embodying the present invention illustrating the basic elements of a stimulation device which can provide cardioversion, defibrillation and pacing stimulation in one or more chambers of the heart.

As illustrated in FIG. 2, a simplified block diagram is shown of the multi-chamber implantable stimulation device 10, which embodies the present invention and is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular electrode 26, the left atrial electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM and/or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As will be seen hereinafter, the processor 60 is set into a static mode when the device is placed into the shelf mode. Hence, while power is still applied to the processor, all internal clocks are turned off to conserve power. Such processor static modes are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the configuration of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing configuration" of the cardiac signal by selectively closing the appropriate switches, as is also known in the art. In this way, the clinician may program the sensing configuration independent of the stimulation configuration.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode configuration, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the activity of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that the recommended replacement time can be determined. Accordingly, the device 10 preferably employs lithium silver vanadium oxide batteries, as is true for most (if not all) defibrillation devices, while devices, which provide only pacing therapy, preferably include lithium iodine batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In accordance with this embodiment of the present invention, the processor 60 further includes shelf mode circuit or stage 77. The shelf mode circuit 77, upon an external command received by the telemetry circuit 100 sets the device 10 in the shelf mode. Once set in the shelf mode, the device 10 is not returned to the fully powered active mode until an externally generated "wake-up" command is received by the telemetry circuit 100. If the device 10 includes defibrillation functionality, while in the shelf mode, the device 10 periodically is returned to an at least partially active mode sufficient to reform the defibrillation output capacitors. Once the capacitors are charged, the shelf mode circuit 77 automatically returns the device 10 to the shelf mode.

To place the device 10 into the shelf mode in accordance with the present invention, the shelf mode circuit disables power to all ancillary circuits of the device. The ancillary circuits include all of the internal circuits of the device 10 except the processor 60, the telemetry circuit 100, a watch dog timer (WDT) 103 and a real time clock (RTC) 101.

The processor 60, while still having power applied to it, is placed into a static state wherein all internal clocks are shut down. Such processor static states are well known in the art. The real time clock 101 continues to be operational for timing capacitor reform periods. To this end, the real time clock may initiate capacitor reformation every six months.

The watch dog timer 103 is of the type well known in the art for servicing and error checking the processor 60. When the device is placed into the shelf mode, the shelf mode circuit 77 decreases the watch dog timer duty cycle to conserve power. Hence, the watch dog timer remains operational, although at a reduced rate, to detect microprocessor errors during the shelf mode.

Lastly, the telemetry circuit 100 is placed into a standby mode. All other sections of the telemetry circuit 100, as for example its transmitting circuits, are disabled from power. This conserves power while maintaining the telemetry circuit 100 in a ready state to receive the externally generated wake-up command for causing the shelf mode circuit to reset the shelf mode and return the device to its fully powered active state.

The foregoing and further aspects of the present invention will become readily apparent from the following description of the flow charts of FIGS. 3–6.

Figure 3:
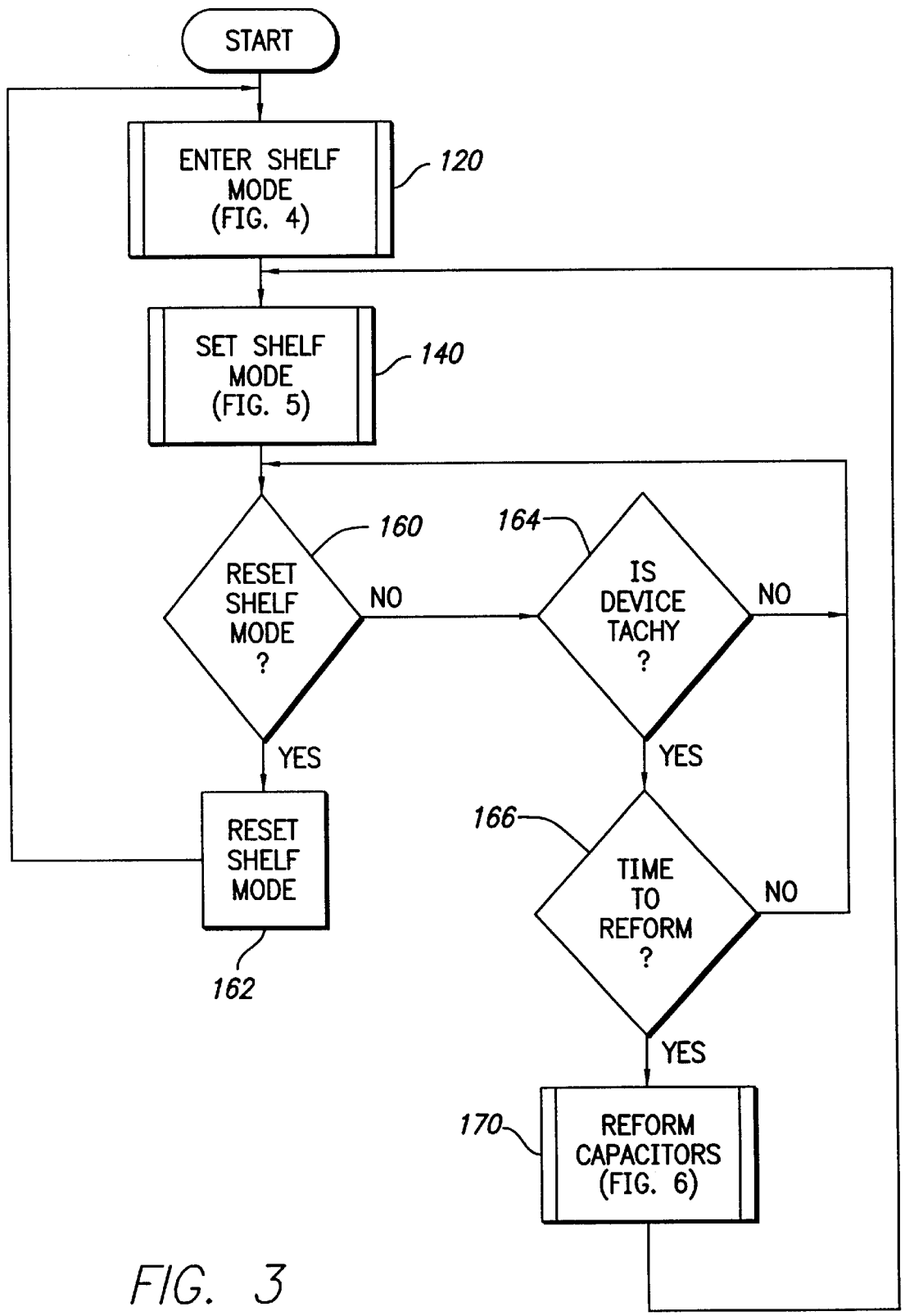
FIG. 3 is a flow chart describing an overview of the operation of one embodiment of the present invention.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the process proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein. Further, unless otherwise stated, all of the specific actions and decisions noted in the flow charts are carried out in hardware to minimize microprocessor intervention. However, the hardware may invoke the microprocessor to execute a specific function or make a decision as appropriate.

The process of FIG. 3 begins with a subroutine 120 for entering the shelf mode. The subroutine 120 will be fully described subsequently with reference to FIG. 4. Basically, the subroutine 120 comprises a series of decision blocks to determine if a genuine externally generated shelf mode command to initiate the shelf mode is received by the telemetry circuit 100. If the shelf mode command criteria are met in subroutine 120, the process proceeds to a subroutine 140 to set the device into the shelf mode.

In subroutine 140, the watch dog timer duty cycle is reduced and the ancillary circuits are disabled from power by the shelf mode circuit 77. Then, unless processor errors are noted by the watch dog timer 103, the subroutine 140 exits after placing the telemetry circuit 100 in the standby mode and the processor 60 in the static state. If processor errors are detected, the shelf mode circuit 77 resets the shelf mode to place the device into a fully powered active state to provide an alert that processor issues must be addressed before the device may be implanted.

Once subroutine 140 is successfully completed and the device 10 is in the shelf mode, all ancillary circuits are disabled from power, the processor 60 is in the static state, the watch dog timer 103 is operating at a reduced rate, the telemetry circuit 100 is in a standby mode only, and the real time clock 101 is fully operational. The device 100 may now be taken out of the shelf mode only under a limited number of conditions. In accordance with this embodiment, these conditions include the receipt of an externally generated wake-up or shelf mode reset command by the telemetry circuit 100 or capacitor reformation. Hence, in decision block 160 the system determines if a reset command has been received. Essentially, the device waits until a reset command is received. If such a reset command is received by the telemetry circuit 100, the telemetry circuit 100 forces the process to advance to activity block 162 for servicing the shelf mode reset command. Here, the telemetry circuit 100 provides the processor with an interrupt to cause the shelf mode circuit 77 to be reset. The shelf mode circuit 77 then proceeds to restore the fully active powered mode by activating all internal clocks, increasing the duty cycle of the watch dog timer 103, applying power to all ancillary circuits, and restoring full functionality to the telemetry circuit 100. The process then returns to subroutine 120 to await receipt of another externally generated shelf mode command.

If the device has not received a shelf mode reset command, has defibrillation functionality noted by decision block 164, and reaches the time for defibrillation capacitor reformation as determined in decision block 166, the process advances to subroutine 170 for reforming the defibrillation capacitors. The subroutine 170 will be described subsequently with respect to FIG. 6. Once the defibrillation capacitors are charged, the process returns to subroutine 140 for placing the device back into the shelf mode. This is performed since capacitor reformation requires the device to be taken out of the shelf mode. However, during capacitor charging, only the circuits that are required for this task are preferably activated.

After returning to and completing subroutine 140, the device will once again be in the shelf mode. It will not be changed from the shelf mode until one of the conditions for resetting the shelf mode is satisfied.

Figure 4:
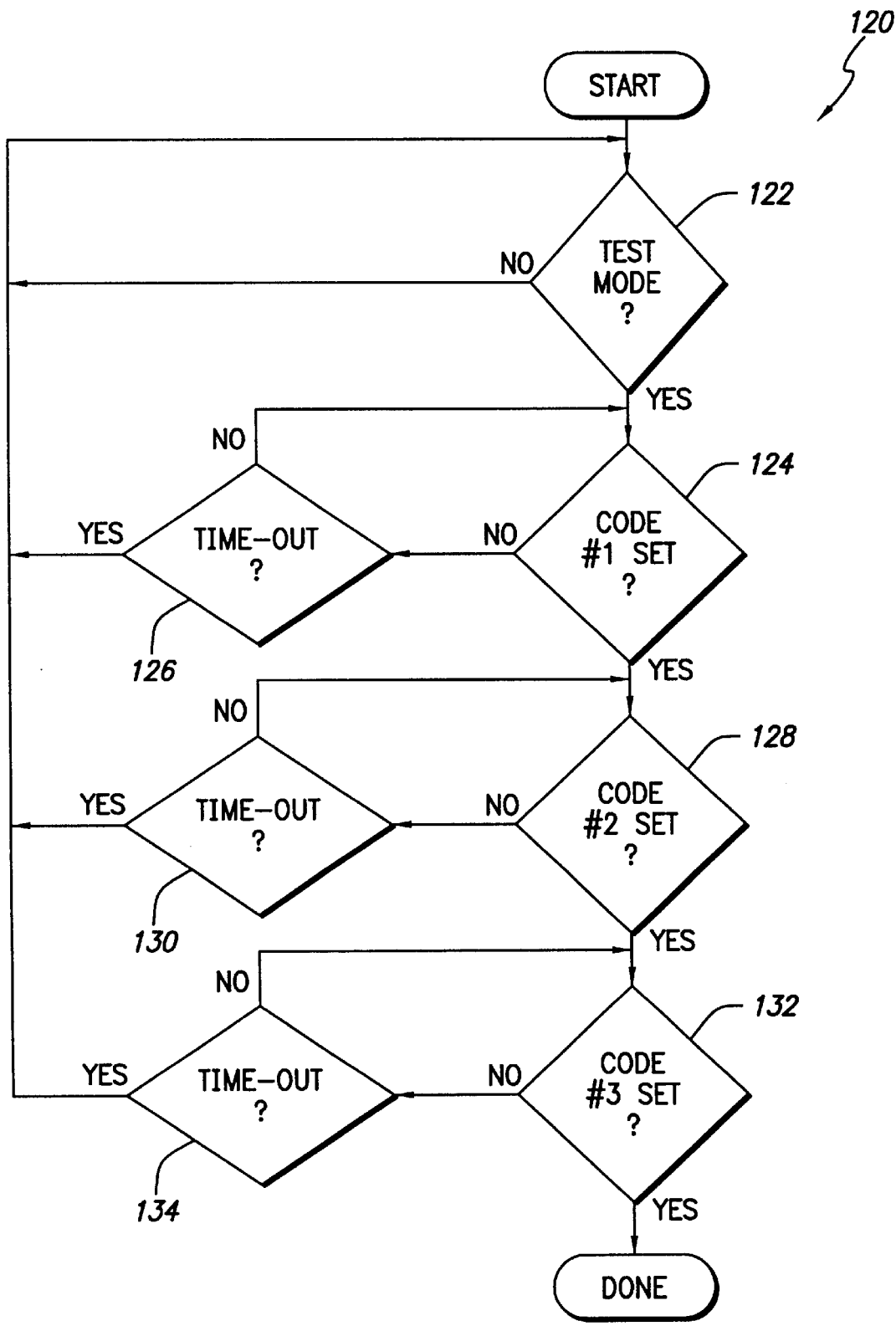
FIG. 4 is a flow chart illustrating the subroutine of FIG. 3 for entering the shelf mode.

The subroutine 120 is shown in FIG. 4. To enter the shelf mode, a genuine shelf mode command must be received by the telemetry circuit 100. A genuine shelf mode command, in accordance with this embodiment of the present invention, requires three codes to be received by the telemetry circuit 100. Each code must be received by the telemetry circuit 100 within a time-out period of, for example, five seconds. First, as noted by the decision block 122, the processor determines if it is in a test mode, meaning that the device is placed into a state allowing the shelf mode command sequence to be initiated. If the processor is not in the test mode, the process returns to decision block 122. If the processor is in a test mode, the process advances to decision block 124 to determine if the first code has been received. If it has not, the processor then determines in decision block 126 if there has been a time-out for receiving the first code. If there has been a time-out for receiving the first code, the process returns. However, if there has not been a time-out for receipt of the first code the process returns to decision block 124. Once the first code is received within its time-out period, the process advances to decision block 128 to determine if the second code has been received.

If the second code has not been received, the process advances to decision block 130 to determine if there has been a time-out for receiving the second code. If there has been a time-out for receiving the second code, the process returns. However, if there has not been a time-out for receiving the second code, the process returns to decision block 128. Once the second code is received within its time-out period, the process advances to decision block 132 to determine if the third code has been received.

If the third code has not been received, the processor then determines in decision block 134 if there has been a time-out for receiving the third code. If there has been a time-out for receiving the third code, the process returns. However, if there has not been a time-out for receiving the third code, the process returns to decision block 132. Once the third code is received within its time-out period, the process completes and the device is now ready to be set into the shelf mode.

Figure 5:
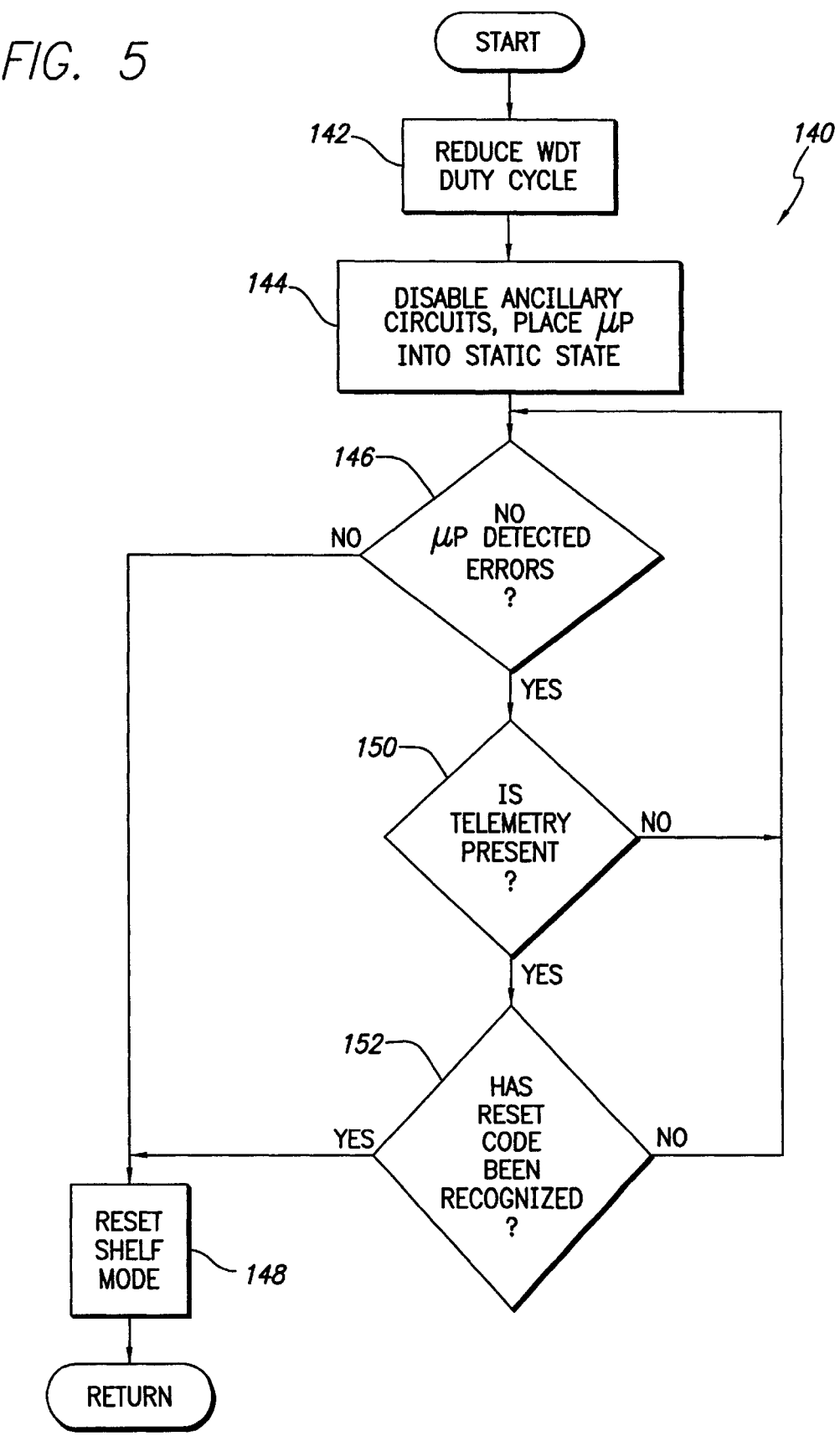
FIG. 5 is a flow chart illustrating the subroutine of FIG. 3 for setting the shelf mode.

The subroutine 140 for setting the device into the shelf mode is shown in FIG. 5. The subroutine 140 begins with an activity block 142 wherein the duty cycle of the watch dog timer 103 is reduced by the shelf mode circuit 77. After the watch dog timer duty cycle is reduced, the process advances to activity block 144 wherein the shelf mode circuit disables the ancillary circuits. As previously mentioned, the ancillary circuits include all of the internal circuitry of the device 10 illustrated in FIG. 2 except for the watch dog timer 103, the real time clock 101, the telemetry circuit 100, and the processor 60.

After power has been removed from the ancillary circuits, in accordance with activity block 144, the process then advances to decision block 146 wherein it is determined if the watch dog timer 103 has detected any processor errors. If processor errors have been detected, the process then advances to activity block 148 wherein the shelf mode is reset. Activity block 148 is carried out by restoring power to the ancillary circuits and restoring the regular duty cycle of the watch dog timer 103. The process then returns.

If, however, it is determined in step 146 that there are no processor errors, the process then proceeds to decision block 150 to determine if telemetry is present. If telemetry is not present, the process then returns to decision block 146 to determine if any processor errors are detected. The device loops between decision blocks 146 and 150 until either telemetry is present or a processor error has occurred. If telemetry is present as determined in decision block 150, the telemetry circuit advances to decision block 152. Decision block 152 interprets telemetry commands to check if a reset code is received and recognized. If not, the process returns to decision block 146. However, if a reset code is recognized, the process advances to activity block 148 for resetting the shelf mode. Once the reset is complete, the process returns. Hence, in accordance with this embodiment, the shelf mode may be reset under any one of three conditions: (1) a recognized reset code; (2) capacitor reformation; and (3) detection of a microprocessor error.

Figure 6:
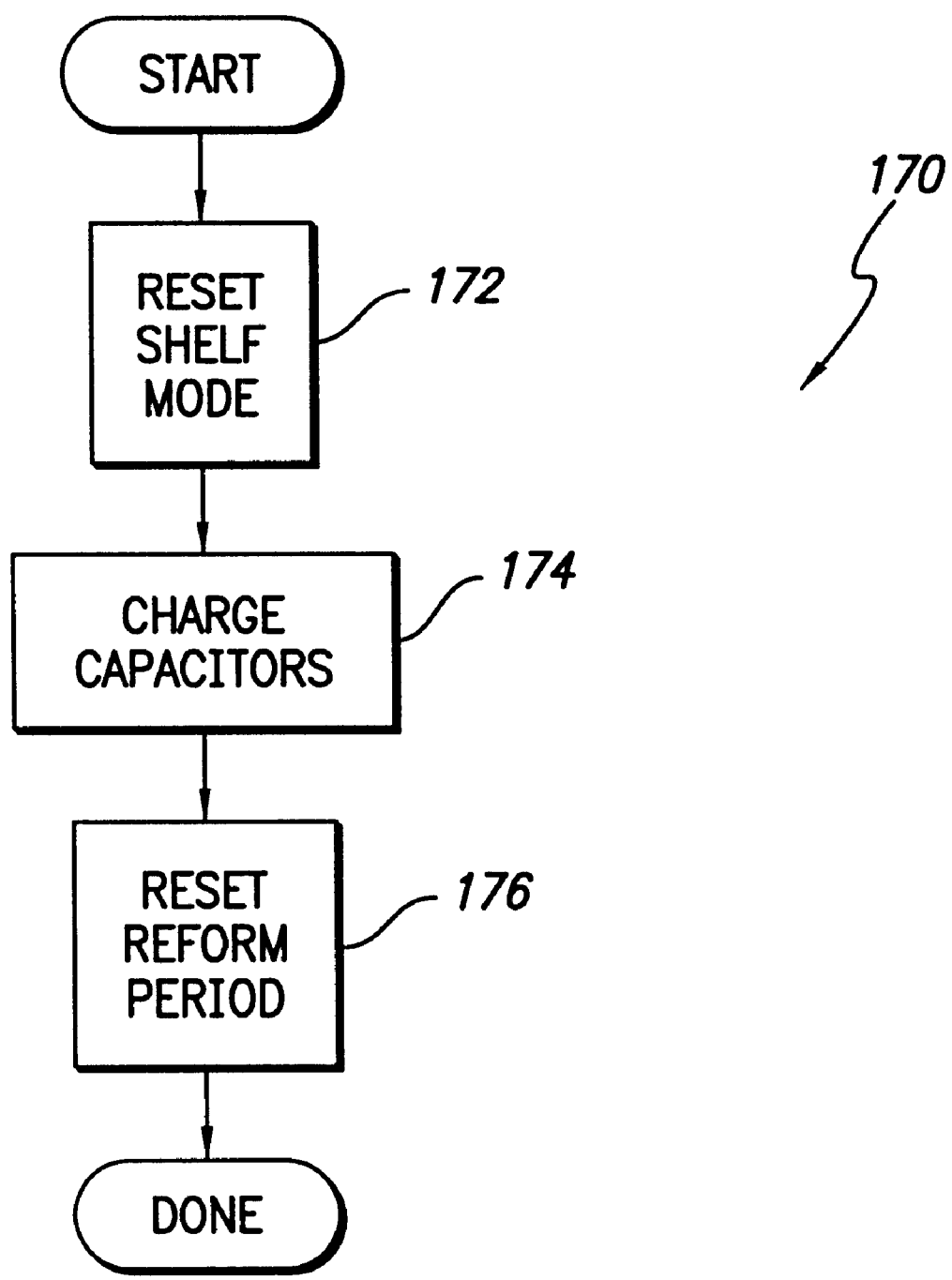
FIG. 6 is a flow chart illustrating the subroutine of FIG. 3 for reforming capacitors of the defibrillator of FIG. 2.

FIG. 6 shows the subroutine 170 for reforming the defibrillation capacitors of the device 10. The subroutine 170 initiates with an activity block 172 wherein the device is reset from the shelf mode. This reset restores sufficient functionality to the ancillary circuits to enable the reformation of the defibrillation capacitors. Once the device is capable of reforming the defibrillation capacitors, the process then proceeds to activity block 174 wherein the defibrillation capacitors are charged. Once the defibrillation capacitors are charged, the process advances to activity block 176 wherein the reform period maintained by the real time clock 101 is reset. As previously mentioned, the capacitor reform period may be six months, for example. Upon completion of activity block 176, the subroutine 170 is completed and the process then returns to subroutine 140 for returning the device to the shelf mode.

As thus may be seen, the present invention provides an implantable cardiac stimulation device, which may be placed into a shelf mode that extends the shelf life of the device. Since all ancillary internal circuitry of the device is disabled from power, very low power consumption is obtained. More particularly, only the real time clock remains fully active while the processor is placed in a static state, the watch dog timer duty cycle is reduced, and the telemetry circuit is placed into a standby mode only. This enables current consumptions on the order of only one microampere or less resulting in a potential pacemaker shelf life of approximately 8 years and a defibrillator shelf life of approximately 4 years.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise then as specifically described herein.

What is claimed is:

1. A processor controlled implantable cardiac stimulation device having a processor, a real-time clock circuit, a watch dog timer circuit having a duty cycle, a telemetry circuit capable of operation in either an active mode or a standby mode, and ancillary circuits that sense cardiac activity and provide stimulation pulses to a heart, the device comprising:
   a power source for providing power to all of the circuits of the device; and
   a shelf mode circuit that disables power to the ancillary circuits, decreases the duty cycle of the watch dog timer, sets the processor into a static state, and sets the telemetry circuit to the standby mode in response to shelf mode commands received by the telemetry circuit to set the device from an active powered mode to a shelf mode and reduce shelf current consumed by the device;
   wherein the watch dog timer remains operational at a reduced rate to detect processor errors during the shelf mode; and
   wherein a transmitting circuit of the telemetry circuit is disabled during the shelf mode and a receiving circuit of the telemetry circuit remains active during the shelf mode.

2. The device of claim 1 further including a decoder circuit that enables the shelf mode circuit upon receiving from the telemetry circuit a plurality of predetermined serial commands.

3. The device of claim 2 wherein the decoder circuit enables the shelf mode circuit when each of the serial commands is received within a preset time.

4. The device of claim 1 wherein the device is an implantable defibrillator having a plurality of capacitors requiring periodic reforming and wherein the device includes a reform circuit that periodically charges the capacitors.

5. The device of claim 1 wherein the shelf mode circuit returns the device to the active powered mode in response to a reset command received by the telemetry circuit.

6. The device of claim 1 wherein the shelf current consumed by the device when the device is in the shelf mode is on the order of one microampere.

7. A processor controlled implantable cardiac stimulation device having a processor, a real-time clock circuit, a watch dog timer circuit having a duty cycle, a telemetry circuit capable of operation in either an active mode or a standby mode, and ancillary circuits that sense cardiac activity and provide stimulation pulses to a heart, the device comprising:
   a power source for providing power to all of the circuits of the device; and
   a shelf mode circuit that disables power to the ancillary circuits, decreases the duty cycle of the watch dog timer, sets the processor into a static state, and sets the telemetry circuit to the standby mode in response to shelf mode commands received by the telemetry circuit to set the device from an active powered mode to a shelf mode and reduce shelf current consumed by the device;
   wherein the device is an implantable defibrillator having a plurality of capacitors requiring periodic reforming and wherein the device includes a reform circuit that periodically charges the capacitors; and
   wherein the reform circuit causes the shelf mode circuit to return the device to the active powered mode prior to reforming the capacitors and causes the shelf mode circuit to reassert the shelf mode after charging the capacitors.

8. An implantable cardiac stimulation device including processing means for controlling operation of the device, real-time clock means for providing clock signals to the processing means, watch dog timer means operable at a duty cycle rate for detecting malfunction of the processing means, telemetry means for receiving external commands when in an active state and wake-up commands when in a standby state, therapy means for sensing cardiac activity and providing stimulation pulses to a heart, and depletable power supply means for supplying power to the processing means, the real-time clock means, the watch dog timer means, the telemetry means and the therapy means, an arrangement for placing the device into a shelf mode from a fully activated powered mode and reducing shelf current consumed by the device, the arrangement comprising shelf mode establishing means for disabling supply of power to the therapy means, decreasing the duty cycle of the watch dog timer means, setting the processor into a static state, and setting the telemetry means to the standby state responsive to shelf mode commands received by the telemetry means for placing the device into the shelf mode;
   wherein the watch dog timer means remains operational at the reduced duty cycle to detect processor errors during the shelf mode; and
   wherein a transmitting circuit of the telemetry means is disabled during the standby state and a receiving circuit of the telemetry circuit remains active during the standby state.

9. The device of claim 8 further including decoder means for enabling the shelf mode establishing means responsive to the telemetry means receiving plurality of predetermined serial commands.

10. The device of claim 9 wherein the decoder means enables the shelf mode establishing means responsive to each of the serial commands being received by the telemetry means within a preset time.

11. The device of claim 8 wherein the device is an implantable defibrillator having a plurality of capacitors requiring periodic reforming and wherein the arrangement includes reform means for periodically charging the capacitors.

12. The device of claim 8 wherein the shelf mode establishing means returns the device to the fully active powered mode responsive to a reset command being received by the telemetry means.

13. The device of claim 8 wherein the shelf current consumed by the device when the device is in the shelf mode is on the order of one microampere.

14. An implantable cardiac stimulation device including processing means for controlling operation of the device, real-time clock means for providing clock signals to the processing means, watch dog timer means operable at a duty cycle rate for detecting malfunction of the processing means, telemetry means for receiving external commands when in an active state and wake-up commands when in a standby state, therapy means for sensing cardiac activity and providing stimulation pulses to a heart, and depletable power supply means for supplying power to the processing means, the real-time clock means, the watch dog timer means, the telemetry means and the therapy means, an arrangement for placing the device into a shelf mode from a fully activated powered mode and reducing shelf current consumed by the device, the arrangement comprising shelf mode establishing means for disabling supply of power to the therapy means, decreasing the duty cycle of the watch dog timer means, setting the processor into a static state, and setting the telemetry means to the standby state responsive to shelf mode commands received by the telemetry means for placing the device into the shelf mode;

wherein the device is an implantable defibrillator having a plurality of capacitors requiring periodic reforming and wherein the arrangement includes reform means for periodically charging the capacitors; and wherein the reform means causes the shelf mode establishing means to return the device to the fully active powered mode prior to reforming the capacitors and causes the shelf mode establishing means to reassert the shelf mode after charging the capacitors.

15. In a processor controlled implantable cardiac stimulation device having a real-time clock circuit, a watch dog timer circuit having a duty cycle, a telemetry circuit capable of operation in either an active mode or a standby mode, ancillary circuits that sense cardiac activity and provide stimulation pulses to a heart, and a power source that provides power to all of the circuits, a method of setting the device from an active powered mode to a shelf mode for reducing shelf current consumed by the device, the method including the steps of:

receiving a shelf mode command signal with the telemetry circuit; and responsive to receiving the shelf mode command signal, placing the device into the shelf mode by disabling power to the ancillary circuits, decreasing the duty cycle of the watch dog timer, setting the processor into a static state and setting the telemetry circuit in the standby mode;

wherein the watch dog timer remains operational at the decreased duty cycle to detect processor errors during the shelf mode; and wherein a transmitting circuit of the telemetry circuit is disabled during the standby mode and a receiving circuit of the telemetry circuit remains active during the standby mode.

16. The method of claim 15 wherein the placing step is performed responsive to the telemetry circuit receiving a plurality of predetermined serial commands comprising the shelf mode command signal.

17. The method of claim 16 wherein the placing step is performed responsive to each of the serial commands being received by the telemetry circuit within a preset time.

18. The method of claim 15 wherein the device is an implantable defibrillator having a plurality of capacitors requiring periodic reforming and wherein the method further includes the step of charging the capacitors at periodic intervals.

19. The method of claim 15 including the further step of receiving a reset command with the telemetry circuit and returning the device to the fully active powered mode responsive to receiving the reset command with the telemetry circuit.

20. In a processor controlled implantable cardiac stimulation device having a real-time clock circuit, a watch dog timer circuit having a duly cycle, a telemetry circuit capable of operation in either an active mode or a standby mode, ancillary circuits that sense cardiac activity and provide stimulation pulses to a heart, and a power source that provides power to all of the circuits, a method of setting the device from an active powered mode to a shelf mode for reducing shelf current consumed by the device, the method including the steps of:

receiving a shelf mode command signal with the telemetry circuit; and responsive to receiving the shelf mode command signal, placing the device into the shelf mode by disabling power to the ancillary circuits, decreasing the duty cycle of the watch dog timer, setting the processor into static state and setting the telemetry circuit in the standby mode;

wherein the device is an implantable defibrillator having a plurality of capacitors requiring periodic reforming and wherein the method further includes the step of charging the capacitors at periodic intervals; and wherein the reforming step includes the steps of returning the device to the active powered mode prior to reforming the capacitors and replacing the device in the shelf mode after charging the capacitors.

\* \* \* \* \*